(12) United States Patent
Doiron

(10) Patent No.: US 7,207,336 B1
(45) Date of Patent: Apr. 24, 2007

(54) DEVICE FOR HELPING A BABY LATCH ONTO A BREAST FOR USE IN BREASTFEEDING

(76) Inventor: Susan M. Doiron, 4250A Carrollton Dr., Bridgeton, MO (US) 63044

( * ) Notice: Subject to any disclaimer, the term of this patent is extended or adjusted under 35 U.S.C. 154(b) by 174 days.

(21) Appl. No.: 10/718,345

(22) Filed: Nov. 20, 2003

Related U.S. Application Data

(60) Provisional application No. 60/428,186, filed on Nov. 21, 2002.

(51) Int. Cl.
*A61B 19/00* (2006.01)
(52) U.S. Cl. ........................................ 128/898; 128/846
(58) Field of Classification Search ................ 128/846, 128/890, 898; 24/489, 492, 499, 513, 517, 24/519; 604/346
See application file for complete search history.

(56) References Cited

U.S. PATENT DOCUMENTS

| | | | | |
|---|---|---|---|---|
| 3,983,887 A | * | 10/1976 | Chan | 132/277 |
| 4,830,030 A | * | 5/1989 | Busch et al. | 132/212 |
| 5,032,103 A | | 7/1991 | Larsson | 450/37 |
| 5,522,407 A | * | 6/1996 | Kelsey | 132/231 |
| 5,758,672 A | * | 6/1998 | Chou | 132/275 |
| 6,237,599 B1 | * | 5/2001 | Maulding | 128/845 |
| 6,502,262 B1 | | 1/2003 | Piscopo | 5/652 |
| 6,962,519 B1 | * | 11/2005 | Clark | 450/37 |

OTHER PUBLICATIONS

La Leche League International, The Breastfeeding Answer Book, Third Revised Edition, pp. 72-75 and 109.
Wiessinger, D., A breastfeeding teaching tool using a sandwich analogy for latch-on, *J Hum Lact* 1998; 14(1):51-56.

* cited by examiner

*Primary Examiner*—Patricia Bianco
*Assistant Examiner*—Camtu Nguyen
(74) *Attorney, Agent, or Firm*—Grace J. Fishel

(57) ABSTRACT

A compression device for use in helping a woman breastfeed an infant. The device has opposed fingers which are movable towards and apart from each other. Just prior to nursing, compression device is placed over the breast centered on the nipple. The compression device compresses the breast tissue between the opposed fingers to form more of a V-shaped wedge for the mouth of the infant to latch onto. Once the infant has successfully latched onto the breast and nursing is initiated the fingers may be moved apart and compression device removed.

3 Claims, 3 Drawing Sheets

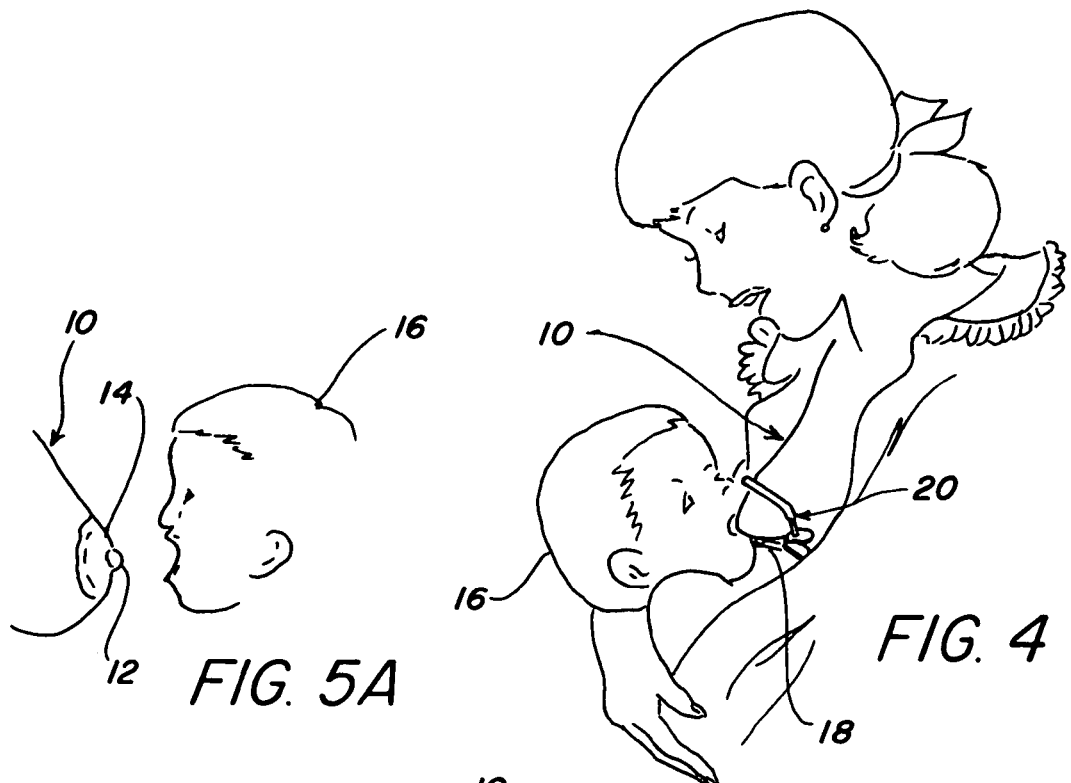
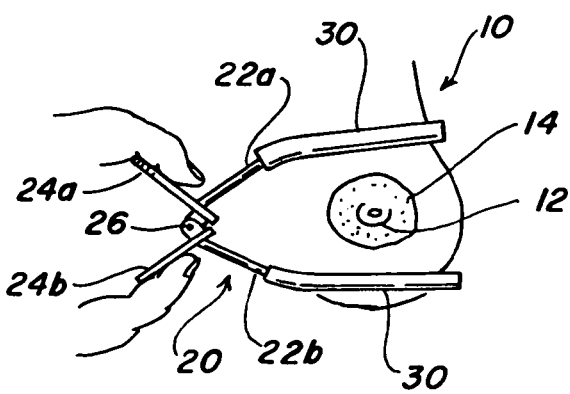
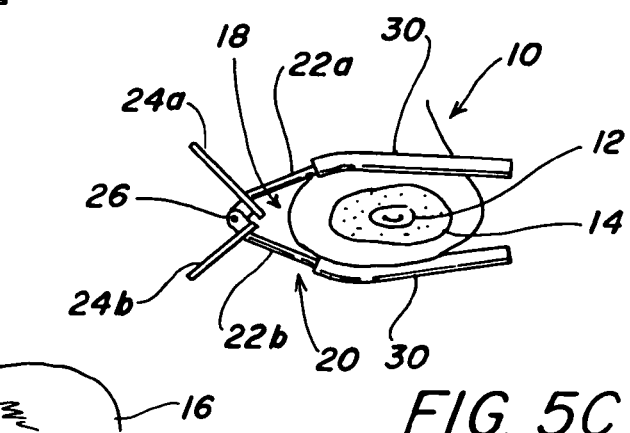
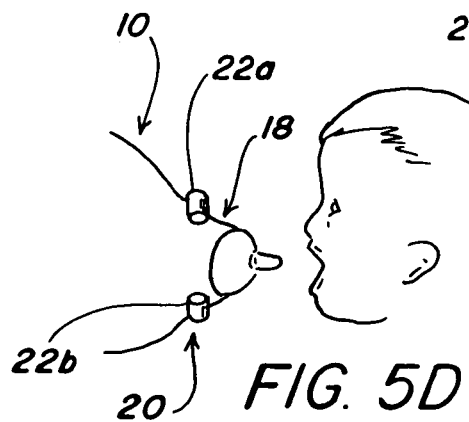
FIG. 4
FIG. 5A
FIG. 5B
FIG. 5C
FIG. 5D

US 7,207,336 B1

DEVICE FOR HELPING A BABY LATCH ONTO A BREAST FOR USE IN BREASTFEEDING

This application claims priority from provisional patent application Ser. No. 60/428,186, filed Nov. 21, 2002, for Assistic Device for Breastfeeding.

BACKGROUND OF THE INVENTION

1. Field of the Invention

The present invention relates to a device for forming a wedge of breast tissue behind a nursing mother's nipple to assist a baby in "latching" onto the breast for breastfeeding.

2. Brief Description of the Prior Art

For nursing mothers, especially with newborn infants, it is often helpful to provide a wedge of the tissue behind the nipple so that the infant can get a better hold of or latch onto the breast. The wedge should be formed so that it's long axis is at an angle aligned with the baby's lips. By modifying the rounded shape of the breast around the nipple into more of a V-shape, the breast is conformed to more readily fit the shape of the baby's open mouth. This allows the infant to obtain a deeper and more effective latch onto the breast tissue for feeding. If the baby is not latched onto the areola behind the nipple, the baby will not only cause trauma to the nipple, but the baby may also not receive a sufficient milk supply. Large breasted mothers and mothers with inverted or flat nipples particularly benefit from making a wedge.

Making a wedge, particularly for first time mothers, is often difficult. It is current practice in the hospital, during the postpartum period, when a baby has trouble latching onto the breast, for a nurse to explain to the mother how to compress her breast with her fingers to form a wedge of the tissue behind the nipple and aligned with the baby's mouth so that the baby can latch on. Due to such stresses as lack of sleep, hormonal changes, emotions, fear of not being successful at nursing, discomfort, family activities, etc., it is often difficult for the new mother to grasp the concept of a manual wedge the first time it is explained, particularly to understand the angle at which the wedge needs to be made. It is not uncommon for the nurse to explain the process several times before the mother understands and is able to make an effective wedge.

If the mother is not able to grasp the concept, a nurse will frequently make the wedge with her fingers with the mother's permission, and sometimes even hold and position the infant, putting the baby on the breast. This may be considered intrusive and may leave the mother feeling inadequate and helpless at a time when she needs all the reassurance that she can get. In addition, it puts a demand on nursing time and increases hospital or institutional costs.

Even if the mother understands the process, there are some angles at which the tissue needs to be wedged that are difficult for the mother to obtain on herself. Also due to the coordination required in breastfeeding including holding the baby, supporting the breast and forming a wedge, an extra set of hands would be useful. Some mothers and infants also have anatomical challenges that make forming a wedge of breast tissue difficult. For example, carpal tunnel syndrome may make it difficult for the mother to make or sustain a hold long enough for the infant to latch on. When the baby has a cleft lip, it may be essential for nursing to form and hold a wedge not only at the initiation of breastfeeding but throughout feeding.

BRIEF SUMMARY OF THE INVENTION

In view of the above, it is an object of the present invention to provide a device that will assist a baby in latching deeply onto a breast. It is another object to provide a device that the mother can use without assistance from others. Other objects and features of the invention will be in part apparent and in part pointed out hereinafter.

In accordance with the invention, a compression device is described for use by a mother in helping a baby deeply latch onto her breast. The device has a pair of opposed fingers adapted to embrace opposite sides of a portion of the breast centered on the nipple and spaced behind the nipple with means for moving said fingers towards each other for compressing the breast tissue behind the nipple to shape the breast into more of a V-shaped wedge whose long axis is generally aligned with the baby's lips. The device also has means for holding said fingers in selected position compressing the breast until the baby latches onto the breast.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which several of various possible embodiments of the invention are illustrated, corresponding reference characters refer to corresponding parts throughout the several views of the drawings in which:

FIG. 4 shows a mother nursing a baby with a compression device forming a generally V-shaped wedge of breast tissue as viewed from the side such that the baby can latch on more effectively;

FIG. 5A illustrates an infant trying to latch onto a woman's rounded breast;

FIG. 5B illustrates a compression device being applied to the breast;

FIG. 5C illustrated the compression device forming a generally V-shaped wedge of tissue behind the nipple;

FIG. 5D illustrates an infant latching onto the breast which has been shaped into a wedge aligned with the infant's lips;

DETAILED DESCRIPTION OF THE INVENTION

Figure 1:
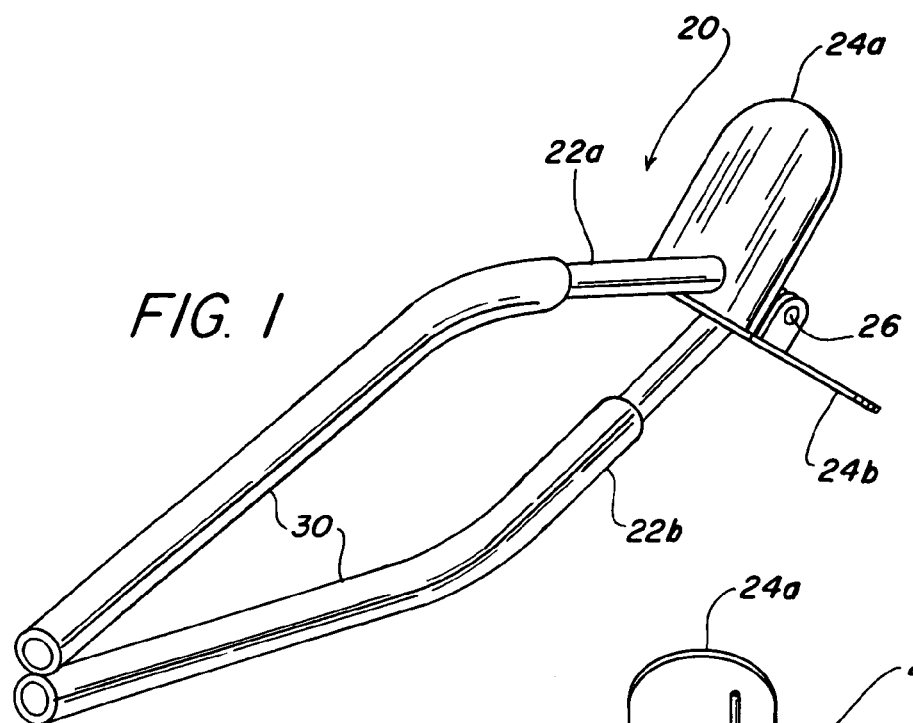
FIG. 1 is a perspective view of a compression device in accordance with the present invention.
Figure 2:
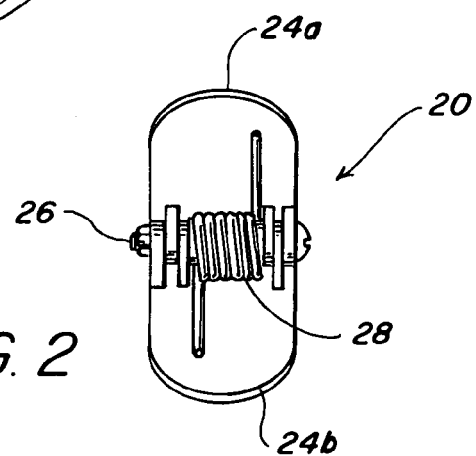
FIG. 2 is an end view of the compression device.

The following detailed description illustrates the invention by way of example and not by way of limitation. This description will clearly enable one skilled in the art to make and use the invention, and describes several embodiments, adaptions, variations, alternatives and uses of the invention, including what is presently believed to be the best mode of carrying out the invention. As various changes could be made in the above constructions without departing from the scope of the invention, it is intended that all matter contained in the description or shown in the accompanying drawings shall be interpreted as illustrative and not in a limiting sense.

Referring to FIG. 5A, a woman's breast 10 has a nipple 12 surrounded by an areola 14. When an infant 16 begins breastfeeding, it is helpful to shape the tissue about nipple 12 just back of nipple 12 into more of a V-shaped wedge 18 as viewed from the side so that infant 16 can more readily latch onto breast 10 and begin feeding as shown in FIG. 5D. A compression device 20 in accordance with the present invention may be used to shape the tissue.

Figure 3:
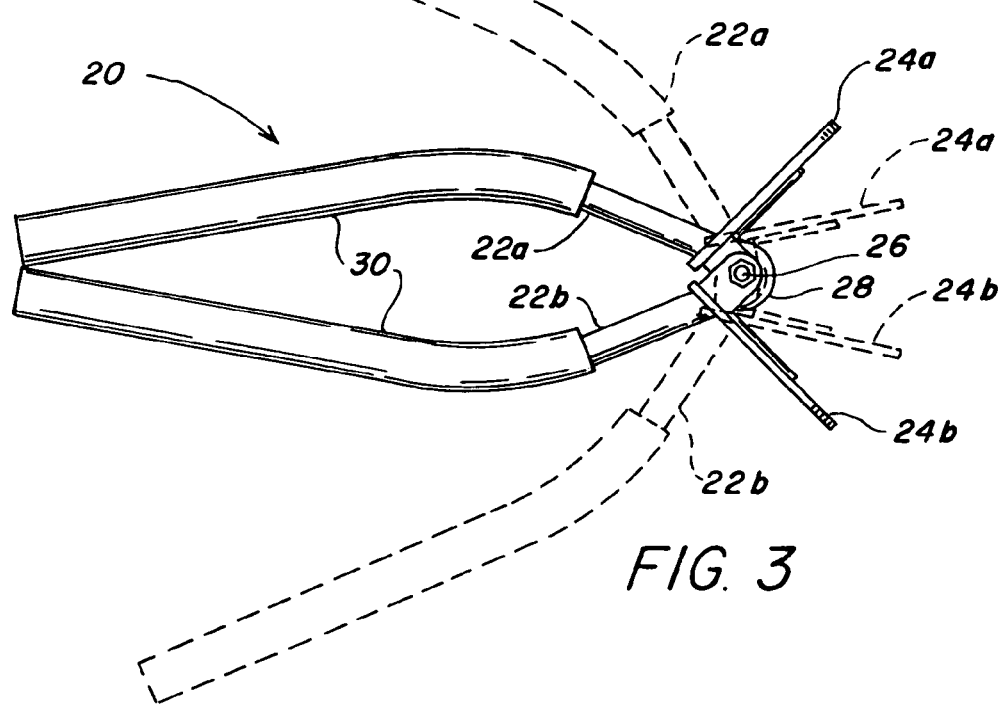
FIG. 3 is a side view of the compression device showing it in open and closed positions.

As shown in FIGS. 1–4 and 5B–5D, compression device 20 comprises a pair of opposed fingers 22a, 22b adapted to embrace opposite sides of a portion of breast 10 centered on nipple 12 and spaced behind nipple 12. Device 20 has means for moving fingers 22a, 22b towards each other for compressing the breast tissue behind nipple 12 to shape the breast into wedge 18, forming a sandwich, whose long axis is generally aligned with the baby's lips. In the form shown in the subject drawings, compression device 20 is a spring clip with a pair of handles 24a, 24b formed as an extension of fingers 22a, 22b for moving fingers 22a, 22b towards and away from each other. Handles 24a, 24b are pivoted together about a pivot pin 26. A spring 28 is attached between handles 24a, 24b forcing fingers 22a, 22b to move towards each other. Finger pressure on the opposite side of handles 24a, 24b urges fingers 22a, 22b apart against the force of spring 28 as shown in FIGS. 3 and 5B. While fingers 22a, 22b are illustrated as movable towards and away from each other by spring pressure, it will be understood by those skilled in the art that fingers 22a, 22b may be ratchet operated or threaded. Tubing 30 or other padding may be applied to fingers 22a, 22b for comfort or for better gripping of the breast tissue. Fingers 22a, 22b may also be flattened, widened or the like to better distribute the force applied to the breast tissue for comfort.

The feeding procedure is such that device 20 is held open by finger pressure and placed over breast 10, centered on and behind nipple 12. As shown in FIG. 5D, this is typically 1 to 2 or more inches behind nipple 12. As finger pressure is released, spring 28 urges fingers 22a, 22b toward each other, compressing the breast tissue to safely and effectively form wedge 18 as best seen in FIGS. 5C and 5D. Once device is in place and wedge 18 formed, infant 16 is brought up against breast 10 so that its mouth will properly engage with breast 10 as shown in FIG. 5D. After infant 16 begins to nurse, device 20 may be removed by engaging handles 24a, 24b and moving fingers 22a, 22b apart.

Initial placement and subsequent removal of device 20 can be done by the woman or someone assisting her. Device 20, which can be either metal, plastic or a combination of materials, does not exert so much pressure on breast 10 that it interferes or has a negative effect on the lactation process. Also, as mentioned above, fingers 22a, 22b may be covered with a soft cushioning material; or, alternatively, made of a soft material. Either way, device 20 is designed and fabricated so as not to cause trauma or discomfort.

Those skilled in the art will understand that device 20 can come in different sizes and with different finger curvatures to accommodate breasts 10 of different sizes and shapes and breast tissue of different firmness. Those skilled in the art will further understand that device 20 should be prepared in an aseptic manner. In hospital settings, the device can have a single use; or, it can have multiple uses if it is used by the same mother and aseptic technique is maintained.

Figure 6:
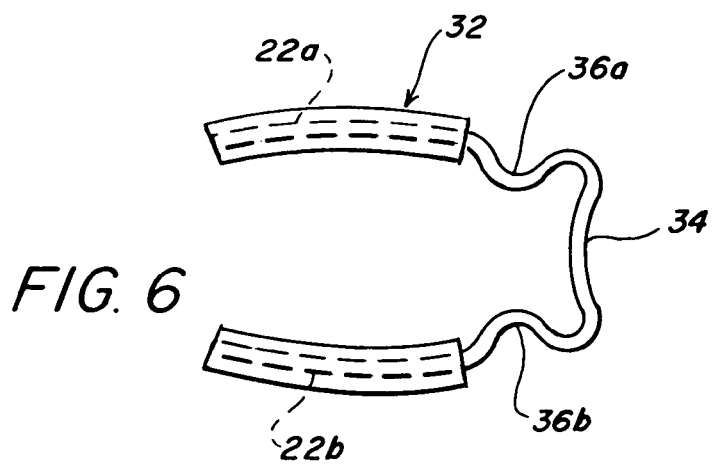
FIG. 6 illustrates a second compression device in accordance with the invention.

Referring to FIG. 6, clip 32 which is variant of compression device 20 and may be formed of molded plastic material. Clip 32 is of a single piece construction with respective fingers 22a, 22b connected by a spring 34, which urges fingers 22a, 22b toward each other to compress breast tissue. Indentations 36a, 36b formed at the inner ends of fingers 22a, 22b allow a user to engage clip 32. When this end of clip 32 is squeezed, fingers 22a, 22b flex away from each other so that clip 32 can be fitted on breast 10 and removed after feeding begins.

Figure 7:
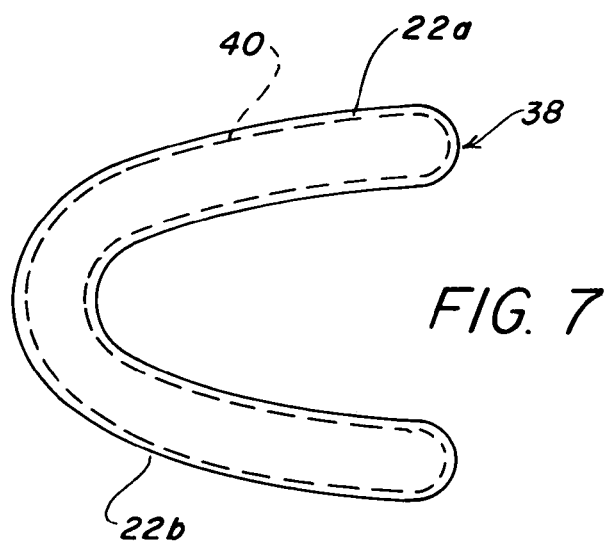
FIG. 7 illustrates a third compression device in accordance with the invention; and, FIG. 8 illustrates a fourth compression device in accordance with the invention.

Referring to FIG. 7, a lightweight, pliable compression device 20 is a generally C-shaped clip 38, which can be formed using a gel material, or a metal. The device can, for example, incorporate a metal stay 40 encased in a gel covering so to provide the necessary cushioning when the device is attached to breast 10. Clip 38 can be made from any type of a cushioned wire or other material pliable enough to create the desired form but with enough stay that when the form is altered it is still able to maintain the compression needed to form wedge 18.

Figure 8:
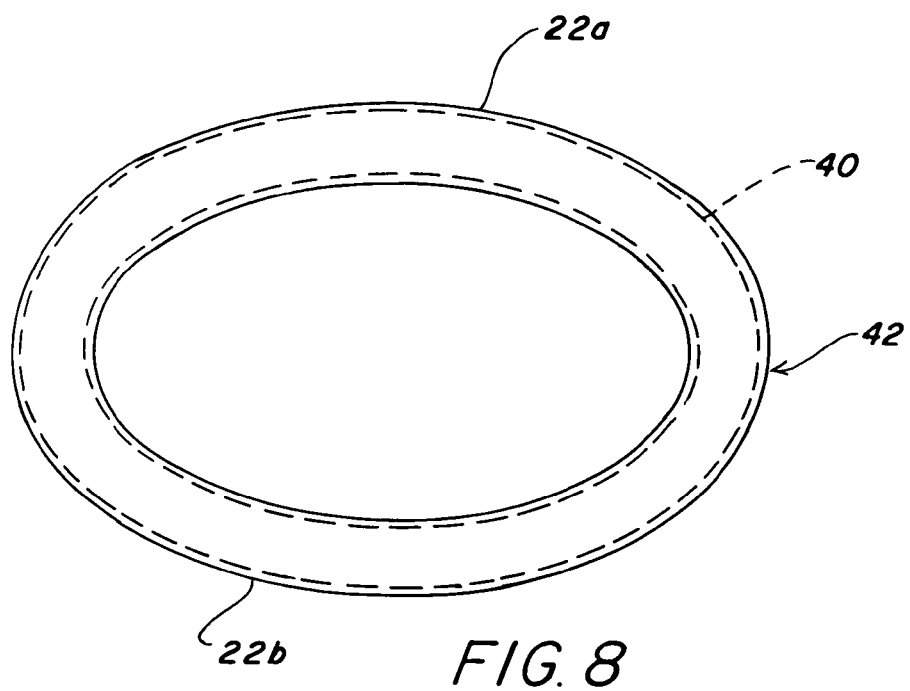

As shown in FIG. 8, compression device 20 can also be formed as an oval loop 42, which fits over breast 10 completely surrounding nipple 12 and spaced behind areola 14. Loop 42 can then be used to compress the tissue behind nipple 12. An advantage of loop 42 is that it equalizes pressure about breast 10 when loop 42 compresses the breast tissue. The inner and outer diameters of loop 42 are a function of the amount of pressure which needs to be applied to provide wedge 18 as previously described. Loop 42 can include a fastener (e.g., a VELCRO fastener, not shown) for opening the loop so that it can be easily installed on and removed from breast 10.

With respect to each of devices 20 described herein, it will be necessary to determine the amount of compression needed for safe usage. This means taking into account the various types and degrees of firmness of breast tissue. Accordingly, there may several models of device 20 to provide a range of compressions, for example from less firm, through moderately firm to very firm. It may be possible for the woman herself to adjust the amount of compression needed to form wedge 18. This can be accomplished, for example by employing a dial, a ratchet device or a gauge setable by the woman to adjust the compression applied by device 20.

What is claimed is:

1. A method for assisting a mother in helping a baby latch onto her breast having a nipple surrounded by an areola, comprising the steps of:

providing a device with a pair of outwardly and oppositely bowed fingers adapted to apply an equalized force on opposite sides of a portion of a breast centered on a nipple and spaced behind the nipple, said device having means for holding said fingers in selected spaced apart position compressing the breast into a V-shaped wedge and making the areola into an oval;

applying said outwardly and oppositely bowed fingers to a breast behind the nipple;

positioning a baby so that its lips are generally parallel with a long axis of a V-shaped wedge of breast compressed by the device; and, allowing a baby to latch onto a breast with an areola flattened by the device into an oval accommodating insertion into a baby's mouth.

2. The method of claim 1 wherein the means for holding said fingers in a selected spaced apart position is a spring attached to the respective fingers for forcing the fingers to move towards each other and a pair of handles formed as an extension of the fingers for moving the fingers away from each other.

3. The method of claim 1 further comprising releasing the breast from the device after a baby has latched.

* * * * *